(12) United States Patent
Fleischman et al.

(10) Patent No.: US 6,447,449 B1
(45) Date of Patent: Sep. 10, 2002

(54) SYSTEM FOR MEASURING INTRAOCULAR PRESSURE OF AN EYE AND A MEM SENSOR FOR USE THEREWITH

(75) Inventors: Aaron J. Fleischman, University Heights; Shuvo Roy, Cleveland, both of OH (US)

(73) Assignee: Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 09/642,573

(22) Filed: Aug. 21, 2000

(51) Int. Cl.[7] ................................................. A61B 3/16

(52) U.S. Cl. ....................................................... 600/405

(58) Field of Search ......................................... 600/405

(56) References Cited

U.S. PATENT DOCUMENTS

| | | |
|---|---|---|
| 4,089,329 A | 5/1978 | Couvillon, Jr. et al. |
| 4,305,399 A | 12/1981 | Beale |
| 4,628,938 A | 12/1986 | Lee |
| 4,922,913 A | 5/1990 | Waters, Jr. et al. |
| 5,005,577 A | 4/1991 | Frankel |
| 5,076,274 A | 12/1991 | Matsumato |
| 5,109,852 A | 5/1992 | Kaye et al. |
| 5,165,409 A | 11/1992 | Coan |
| 5,179,953 A | 1/1993 | Kursar |
| 5,217,015 A | 6/1993 | Kaye et al. |
| 5,375,595 A | 12/1994 | Sinha et al. |
| 5,636,635 A | 6/1997 | Massie et al. |
| 5,830,139 A | 11/1998 | Abreu |

OTHER PUBLICATIONS

Intraocular Pressure Measurement With Instrumented Contact Lenses, Invest. Opthmalmology Report; M.E. Greene, et al.; Apr. 1974, pp. 299–302.

Self–Tonometry To Manage Patients With Glaucoma And Apparently Controlled Intraocular Pressure; J.T. Wilensky, et al.; Arch Opthalmol—vol. 105, Aug. 1987, pp. 1072–1075.

Passive Radiotelemetry Of Intraocular Pressure In Vivo: Calibration And Validation Of Continual Scleral Guard–Ring Applanation Transensors In The Dog And Rabbit; Cooper and Beale et al., Assoc. for Res. in Vis. and Ophthal., Inc. pp. 930–938, vol. 18 No. 9, 1979.

Continual Monitoring Of Intraocular Pressure: Effect Of Central Venous Pressure, Respiration, And Eye Movements On Continual Recordings Of Intraocular Pressure In Rabbit, Dog And Man, Cooper and Beale, et al., British Journal of Ophthalmology, 1979 pp. 799–804.

Radio Telemetry Of Intraocular Pressure In Vitro, Cooper and Beale, Invest. Ophthalmol. Visual Sci. Feb. 1977, pp. 168–171.

(List continued on next page.)

*Primary Examiner*—Eric F. Winakur
*Assistant Examiner*—Pamela L Wingood
(74) *Attorney, Agent, or Firm*—Tarolli, Sundheim, Covell, Tummino & Szabo L.L.P.

(57) ABSTRACT

A tonometer sensor for disposition in proximity to a portion of a surface of eye comprises a substrate including a contact surface for making contact with the surface portion of the eye. The contact surface includes an outer non-compliant region and in inner compliant region fabricated as an impedance element that varies in impedance as the inner region changes shape. A first region of material is responsive to a non-invasive external force to press the contact surface against the surface portion of the eye and cause the compliant region to change shape in proportion to an intraocular pressure of the eye. A second region of conductive material is electrically coupled to the impedance element of the compliant region and is responsive to an external signal for energizing the impedance element so that the intraocular pressure may be determined.

54 Claims, 13 Drawing Sheets

OTHER PUBLICATIONS

Progress In Continual Eye Pressure Monitoring, Cooper, et al., Australian Journal of Ophthalmology, 1983; pp. 143–148.

A New Tonometer Based On The Application Of Micro–Mechanical Sensors, Besten and Bergveld, MESA Research Institute, The Netherlands, 1993, pp. 105–110.

Corneal Bending And Buckling In Tonometry, Marg, Mackay, Oechsli, Archives of Ophthalmology, vol. 4, Jan. 1961, pp. 67–74.

Wireless Micromachined Ceramic Pressure Sensors, English and Allen, School of Elelctrical and Computer engineering, Georgia Institute of Technology, IEEE, 1999, pp. 511–516.

Dynamic Tonometry, Dekking and Coster, Ophthalmologica, 154: 1967, pp. 59–75.

A Rapid Pneumatic Applanation Tonometer, Langham and McCarthy, Arch Opthal vol. 79, Apr. 1968, pp. 389–399.

The Validity Of The Imbert–Fick Law As Applied To Applanation Tonometry, Gloster and Perkins, Exp. Eye Res., vol. 2, May 1963, pp. 274–283.

The Goldman Applanation Tonometer, Moses, pp. 865–869.

Magnetic Microactuation Of Polysilicon Flexure Structures, Judy, Muller and Zappe, 1994, pp. 43–59.

A Theoretical And Experimental Study Of The Mechanical Behavior Of The Cornea With Application To The Measurement Of Intraocular Pressure, Schwartz, MacKay, Sackman, University of California Berkeley, Bulletin of Mathematical Biophysics, vol. 28, 1966, pp. 585–643.

Reliability Of Intraocular Pressure Measurements After Myopic Excimer Photorefractive Keratectomy, Abbasoglu, Bowman, Cavanaugh and McCulley, Ophthalmology, vol. 105, No. 12, Dec. 1998 rev. pp., 2193–2196.

Sources Of Error With Use Of Goldmann–Type Tonometers, Whitacre and Stein, Survey of Ophthalmology, vol. 38. No. 1, Jul.–Aug. 1993, pp. 1–30.

A Noncontact Applanation Tonometer, Forbes, Pico, Jr., Grolman, Arch Ophthalmol. vol. 91, Feb. 1974, pp. 134–140.

Trough Height, Pressure And Flattening In Tonometry, Marg, MacKay & Oechsli, Vision Research, vol. 1, pp. 379–385, 1962.

Fast, Automatic, Electronic Tonometers Based On An Exact Theory, MacKay & Marg, Acta Ophthalmologica, vol. 37, 1959, pp. 495–507.

A New Technique For In Vivo Intraocular Pharmacokinetic, Measurements, Ocular Dialysis, Ben–Nun, Cooper, Cringle, Constable, Arch. Ophthalmol, vol. 106, Feb. 1988, pp. 254–259.

Diurnal Variation In Intraocular Pressure, Phelps, Woolson, et al., and Kolker and Becker, American Journal of Ophthalmology, Mar., 1974, pp. 367–376.

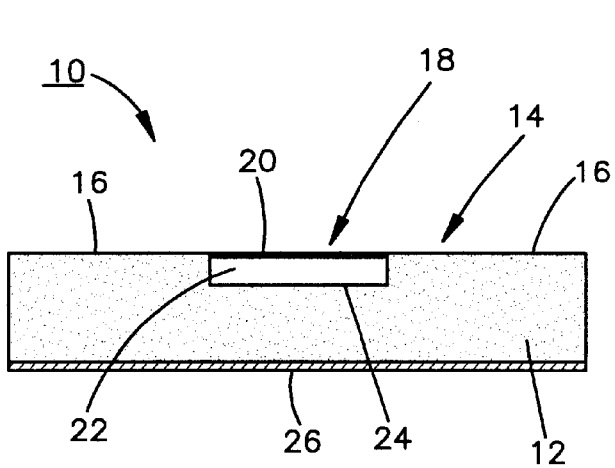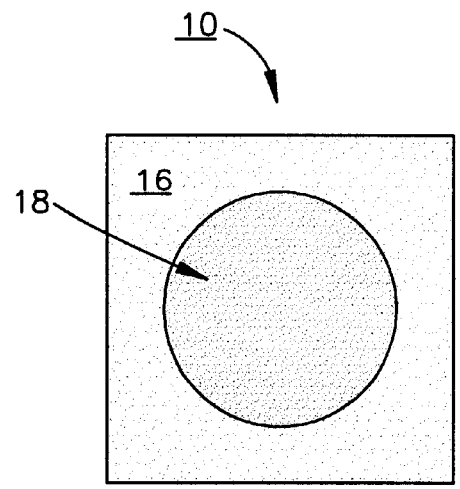
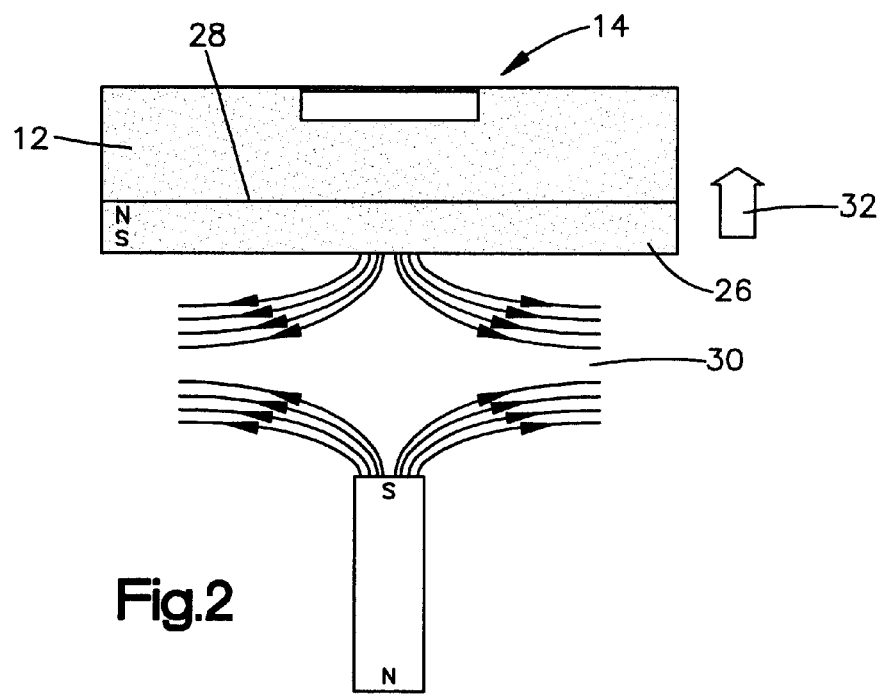

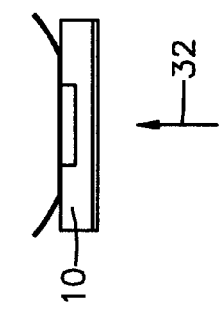
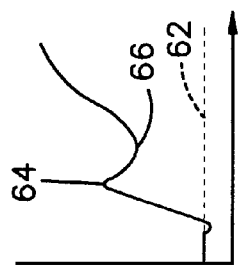
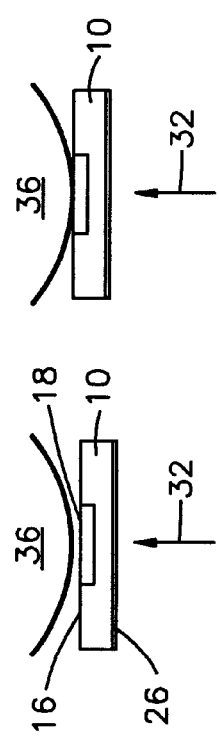
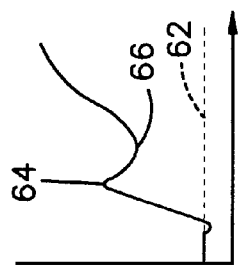
Fig.11(A1) Fig.11(B1) Fig.11(C1) Fig.11(D1) Fig.11(E1)
Fig.11(A2) Fig.11(B2) Fig.11(C2) Fig.11(D2) Fig.11(E2)

SYSTEM FOR MEASURING INTRAOCULAR PRESSURE OF AN EYE AND A MEM SENSOR FOR USE THEREWITH

BACKGROUND OF THE INVENTION

The present invention relates generally to the measurement of intraocular pressure (IOP) of eyes, and more particular, to a microelectromechanical (MEM) tonometer sensor that may be disposed on a flexible contact lens for disposition in proximity to an eye and its use with a portable control unit for non-invasively monitoring the IOP of the eye.

Glaucoma patients and post operative patients of eye surgery require regular monitoring of the IOP of their eyes in order to diagnose degenerative conditions which may lead to degraded sight and/or blindness without immediate medical treatment. Accordingly, such patients must make frequent trips to their ophthalmologist's office for this regular monitoring of their IOP with conventional mechanical impact type tonometers. This becomes a nuisance to the patient after a time leading to patient resistance to compliance. In addition, the only measurement of the patient's IOP that the doctor can use for diagnosis is the pressure that exists at the time of the office visit. Therefore, if the pressure is normal at the time of the visit, but becomes high thereafter, the patient's actual risk of blindness may be misdiagnosed. Also, if the pressure measured at the time of the office visit is high for reasons other than eye degeneration, the patient may be falsely diagnosed and be required to undergo therapy that may not be needed.

Intraocular pressure has been known to fluctuate widely during any given period of time and thus, should be monitored many times during the period of a day in order to gain an average or representative IOP which in turn may be tracked for diagnosis. Attempts have been made to permit glaucoma patients to monitor their IOP at home many times during the period of a day with a self-tonometry portable instrument. Reference is made to the paper "Self-Tonometry to Manage Patients With Glaucoma and Apparently Controlled Intraocular Pressure", Jacob T, Wilensky et al., published in Arch Ophthalmol, Vol. 105, August 1987 for more details of such a device. This paper describes a portable, tonometer instrument consisting of a pneumatically driven plunger, fitted with an elastic membrane, that slowly comes forward and applanates the cornea. Applanation is detected by a internal optic sensor and the pressure necessary to achieve applanation is registered and displayed automatically. The patient is able to prepare the eye and self-tonometer and activate the instrument for taking the measurement. However, the device proposed is relatively large and bulky, about the size of an attache' case, for example, and not conducive to convenient transport with the patient during normal daily routine in order to measure IOP. In addition, the proposed technique requires special eye preparation by instilling a topical anesthetic in the eye prior to tonometric measurements.

Also, very crude attempts have been made to develop methods of non-invasively monitoring IOP using passive electronic circuitry and radiotelemetry disposed at the eye. In the papers of R. L. Cooper et al. namely those published in Invest, Ophthalmol Visual Sci, pp. 168–171, February 1977; British JOO, 1979, 63, pp. 799–804; Invest, Ophthalmol Visual Sci., 18, pp. 930–938, September, 1979; and Australian Journal of Opthalmology 1983, 11, pp. 143–148, a miniature guard ring applanating transsensor (AT) which included electronic components that changed in resonance proportional to the IOP was mounted in an acrylic or sauflon haptic contact lens element that was individually designed for the human eye. The AT was mounted in the lower part of the scleral haptic so that it applanated the inferior sclera under the lower lid. The whole haptic ring was placed in the conjunctival fornix. IOP was monitored from the AT with an automatic continual frequency monitor (ACFM) attached by adhesive and elastic bands to the exterior of the lower eye lid. The ACFM induced in the AT electromagnetic oscillations at varying radio frequencies via a magnetic coupling of inductive coils and monitored for its resonant frequency representative of IOP. This device is clearly uncomfortable and bulky, minimizing expected patient compliance. In addition, the device measures IOP by applanation of the sclera, which is a rather unconventional method of measuring IOP.

In another paper reported in Investigative Ophthalmology Reports, pp. 299–302, April, 1974 by B. G. Gilman, a device is presented for measuring IOP of a rabbit in a continuous manner with strain gauges mounted (imbedded) in soft flush fitting, silastic gel (hydrogel) contact lenses. The exact shape of the eye of the rabbit was obtained by a molding procedure. Leads of the strain gauges extended from the lens and were connected to a wheatstone bridge arrangement for measurement taking. The paper suggests that the imbedded strain gauges may be used with a miniature telemetry package completely contained in a hydrophilic hydrogel contact lens for continuous, noninvasive, long duration monitoring of IOP, albeit no design was provided. This device proposes wire connections for telemetry which entails wires to be run out of the eye under the eyelid. Also, the proposed approach requires the molding of a special contact for each individual eye, a practice which would make widespread use unattractive and expensive.

In 1993, an IEEE paper was presented by C. den Besten and P. Bergveld of the University of Twente, The Netherlands, proposing a new instrument for measuring area of applanation entitled "A New Tonometer Based On The Application of Micro-Mechanical Sensors". This new instrument is based on the Mackay-Marg principle of tonometer operation in which a plate having a diameter of 6 mm or less is pressed against and flattens a portion of the cornea of the eye, referred to as "applanation". In the middle of the plate is a small pressure sensitive area that is pressed against the flattened portion of the cornea with a slowing increasing force while the pressure area is electronically measured. The applanation sensor of this new instrument comprises a micro-machined plunger and pressure sensing electronics on three electrically insulated levels of a silicon substrate resulting in a modified Mackay-Marg tonometer in which the radius of the flattened area and the distance between the periphery of the applanation and the pressure center can be measured to render a more accurate pressure area measurement. In the work presented in this paper, the researchers did not actually propose a pressure sensor or transducer. In addition, it is not clear that as long as the eye is applanated, there is a need to know the area of applanation. Sufficient applanation is usually determined by the difference in trough height from the peak to dip of the pressure profile. The dip is unlikely to occur unless sufficient applanation is achieved.

Also, in the U.S. Pat. No. 5,830,139; entitled "Tonometer System for Measuring Intraocular Pressure by Applanation and/or Indentation"; issued to Abreu on Nov. 3, 1998, a tonometer system is disclosed using a contact device shaped to match the outer surface of the cornea and having a hole through which a movable central piece is slidably disposed for flattening or indenting a portion of the cornea. A magnetic field controls the movement of the central piece against the eye surface to achieve a predetermined amount of applanation. A sophisticated optical arrangement is used to detect when the predetermined amount of applanation has been achieved to measure IOP and a calculation unit determines the intraocular pressure based on the amount of force the contact device must apply against the cornea in order to achieve the predetermined amount of applanation. The magnetic and optical arrangements of this device requires special alignment and calibration techniques rendering it difficult for use as a self-tonometry device.

While the various foregoing described U.S. patent and papers propose various devices and instruments for tonometry, none appears to offer a viable inexpensive, convenient solution to the immediate problem of self-tonometry. The present invention overcomes the drawbacks of the proposed instruments described above to yield a simple, inexpensive and easy to use instrument that completely automates the tonometry process and offers post processing of tonometer IOP readings from which a proper evaluation and diagnosis by an ophthalmologist may be performed.

SUMMARY OF THE INVENTION

In accordance with one aspect of the present invention, a tonometer sensor for disposition in proximity to a portion of a surface of an eye comprises: a substrate including: a contact surface for making contact with the surface portion of the eye, the contact surface including an outer non-compliant region and an inner compliant region fabricated as an impedance element that varies in impedance as said inner region changes shape; a first region of material responsive to a non-invasive external force to press the contact surface against the surface portion of the eye and cause the compliant region to change shape in proportion to an intraocular pressure of the eye; and a second region of conductive material electrically coupled to the impedance element of the compliant region and responsive to an external signal for energizing the impedance element so that the intraocular pressure may be determined.

In accordance with another aspect of the present invention, a flexible contact lens including a tonometer sensor for disposition in proximity to a portion of a surface of an eye comprises: a surface contoured to the surface of the eye for disposition in proximity thereto; and the substrate of the tonometer sensor disposed at the lens surface and oriented such that the contact surface of the substrate will be juxtaposed with the surface of the eye when the lens is disposed in proximity thereto.

In accordance with yet another aspect of the present invention, A tonometer system comprises: the flexible contact lens including a surface contoured to a portion of a surface of an eye for disposition in proximity thereto; the tonometer sensor including the substrate disposed at the lens surface; and a control unit positionable in proximity to the tonometer sensor for generating the non-invasive force signal over a predetermined time interval and for generating the activation signal to measure a signal representative of the intraocular pressure.

In accordance with still another aspect of the present invention, a method of measuring intraocular pressure (IOP) of an eye with a flexible contact lens having a microelectromechanical (MEM) sensor affixed thereto comprises the steps of: disposing the contact lens in close proximity to a surface of the eye with a surface of the MEM sensor in juxtaposition with the eye surface; generating a non-invasive force which presses and releases the compliant region of the surface of the MEM sensor against and from the surface of the eye in accordance with a predetermined force vs. time envelope causing the compliant region that is fabricated as an impedance element to change shape and vary in impedance as a result thereof; energizing the impedance element a multiplicity of times during said force vs. time envelope; determining a pressure representative measurement each time the impedance element is energized; and processing the pressure representative measurements to render a resultant IOP measurement.

BRIEF DESCRIPTION OF THE DRAWINGS

FIGS. 1A and 1B are cross-sectional and plan views of a MEM tonometer sensor suitable for embodying the principles of the present invention.

FIG. 2 is a cross-sectional illustration the MEM tonometer sensor responding to a magnetic field.

FIGS. 11A–11E are exemplary illustrations of the response of the MEM tonometer sensor embodiment to the envelope of the magnetic field over time suitable for explaining the operation of the system embodiment of FIG. 8.

DETAILED DESCRIPTION OF THE INVENTION

Figure 3A:
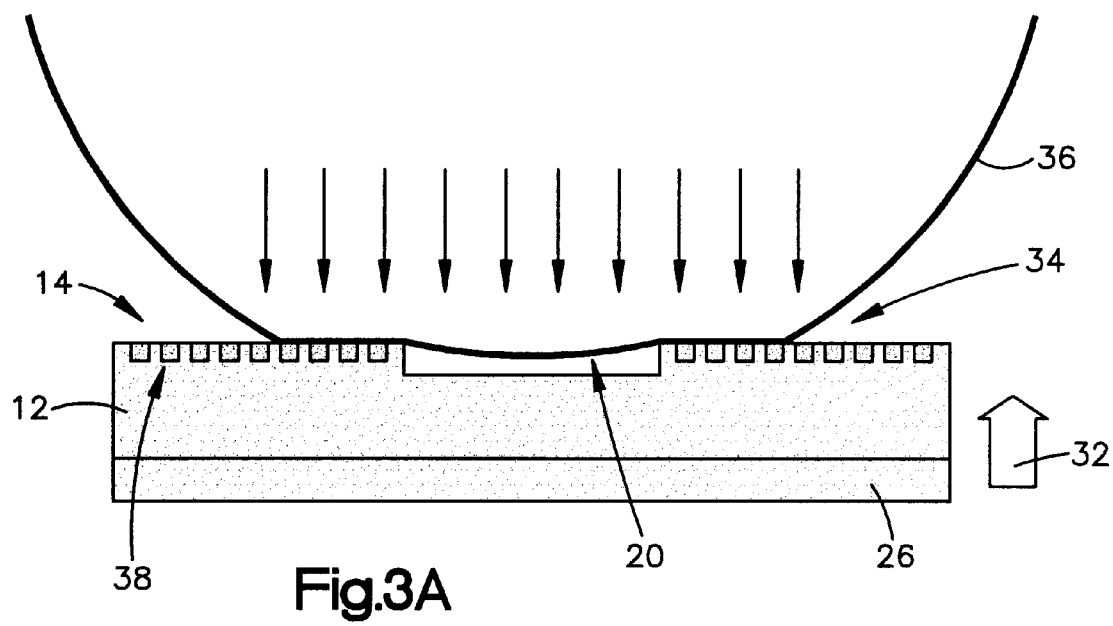
FIGS. 3A and 3B are cross-sectional and plan views of the tonometer sensor embodiment revealing additional regions in accordance with the principles of the present invention.

A tonometer sensor 10 of the microelectromechanical (MEM) variety is shown in cross-sectional and plan views in FIGS. 1A and 1B, respectively. The tonometer sensor 10 includes a substrate 12 which, for the present embodiment, may be comprised of a Silicon material, for example, but it is understood that other materials may be used just as well.

The substrate 12 includes a contact surface 14 for making contact with a portion of a surface of an eye (not shown). The surface 14 includes an outer non-compliant region 16 and an inner compliant region 18 that is fabricated using microelectromechanical techniques (which will be described in greater detail herein below) as an impedance element, the impedance of which varying as the inner region 18 changes shape. In the present embodiment, the compliant region 18 comprises a diaphragm 20 as one plate of a capacitive element that is separated by a dielectric 22 from an other plate 24 of the capacitive element which is part of the non-compliant region 16. As will become more evident from the description below, as the contact surface 14 is pressed against the surface portion of the eye, the diaphragm plate 20 flexes closer to the other non-compliant plate 24 to change the capacitance of the capacitive element in proportion to the IOP of the eye. Also, in this embodiment, the dielectric comprises air, but other possible suitably compliant dielectrics may be used such as hydrogel and silicone, for example, without deviating from the principles of the present invention.

Another region of material 26 is included in the substrate 12 to be responsive to a non-invasive external force to press the contact surface 14 against the surface portion 34 of the eye 36 and cause the compliant region or diaphragm 20 to change shape in proportion to the IOP of the eye (refer to FIG. 3A). In the present embodiment, the region 26 comprises a region of magnetic material responsive to a magnetic field 30 as shown by the illustration of FIG. 2. Referring to FIG. 2, a surface 28 of the substrate 12 opposite the contact surface 14 is layered with a magnetic material that forms a permanent magnet 26 with its North-South poles aligned along an axis transverse to the contact surface 14. For this example, the magnetic material may include plated Permalloy, plated iron, plated CoNiMnP, a screen printed polymer composite, and rolled magnetic films. A process for layering the magnetic material 26 to the surface 28 for the present embodiment will be described in greater detail herein below. Accordingly, as the magnetic field 30 is brought in proximity to the permanent magnet layer 26 as shown in FIG. 2, the substrate 12 is repulsed by the magnetic field 30 with a force 32. The strength of the magnetic field 30 determines the force 32 at which the contact surface 14 is pressed against the surface portion 34 of the eye 36 as shown by the illustration of FIG. 3A.

Figure 3B:
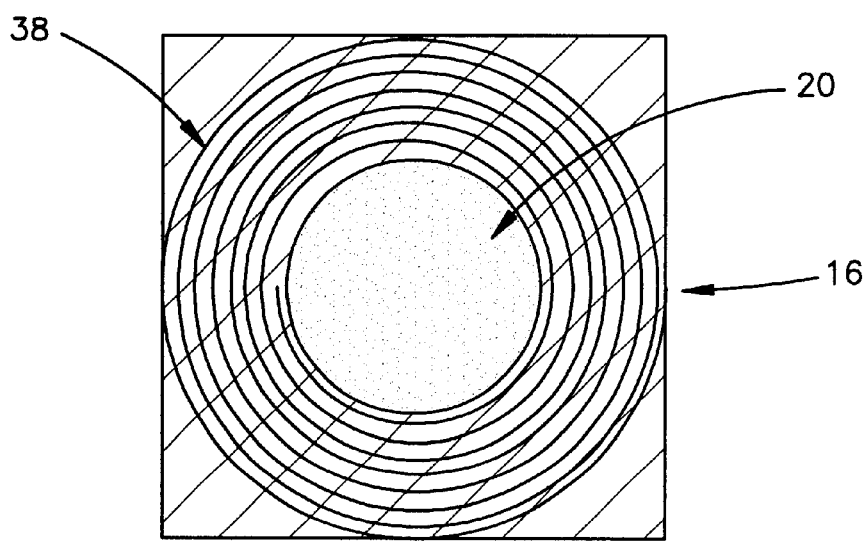

As shown by the substrate cross-sectional and plan views of FIGS. 3A and 3B, a region of conductive material 38 is included as part of the substrate 12 and is electrically coupled to the impedance element of the compliant region or diaphragm 20 which is a capacitive element in the present example. While not shown in the FIGS. 3A and 3B, this electrical coupling will be described in greater detail in connection with the fabrication drawings found herein below. The conductive material 38 is responsive to an external signal for energizing the impedance element so that the IOP may be determined as will become more evident from the description found herein below. In the embodiment shown by the views of FIGS. 3A and 3B, the conductive region 38 comprises an inductor coil fabricated in the non-compliant region 16 of the contact surface 14 such that it is electrically coupled to the capacitive element to form a resonance or tank circuit. In the present embodiment, the inductor coil 38 is formed by disposing conductive material in a predetermined pattern, like a concentric spiraled pattern, for example, at the non-compliant region 16. A process for fabricating the inductor coil 38 at the region 16 will be described in greater detail herein below. However, it is understood that the inductor region need not be embodied solely at the non-compliant region and may be embodied as part of the compliant region as well without deviating from the broad principles of the present invention.

In the present embodiment, the resonant circuit comprising the coil 38 and capacitive element formed by the plates 20 and 24 may be excited into resonance by an external electromagnetic signal in the radio frequency (RF) range. Tank circuits of this type have a natural resonant frequency $f_0$ that to the first order depends of the values of the inductor and capacitor as follows:

$$f_0 = \frac{1}{2}\pi (LC)^{1/2},$$

where L is the inductance and C is the capacitance. It is intended that during the fabrication process any parasitic resistance will be kept to a minimum so as to not significantly affect the natural frequency according to the above expression. Accordingly, as the capacitance of the tonometer sensor changes, the resonant frequency $f_0$ of the tank circuit will change in proportion thereto.

For example, if the contact area 14 of the tonometer sensor is approximately one square millimeter (1 mm$^2$) or one millimeter (1 mm) on each side, the diaphragm of the compliant region may have a diameter of five hundred micrometers (500 $\mu$m) with a one and a half micrometer (1.5 $\mu$m) dielectric or air gap, and the inductor coil may have twenty five (25) turns with an ID of five hundred micrometers (500 $\mu$m) and an OD of one thousand micrometers (1,000 $\mu$m), then with the diaphragm undisturbed, the resonant frequency may be on the order of one hundred and ninety-three megahertz (193 MHz). Accordingly, a ten percent (10%) increase in capacitance, for example, resulting from a diaphragm deflection will produce a downward shift in resonant frequency to one hundred and eighty-four point one megahertz (184.1 MHz) and this shift in resonant frequency is readily discernible electronically as will be further described herein below. It is understood that the contact area of the sensor may be less than 1 mm in which case, the various dimensions may be rescaled proportionately.

Figure 4:
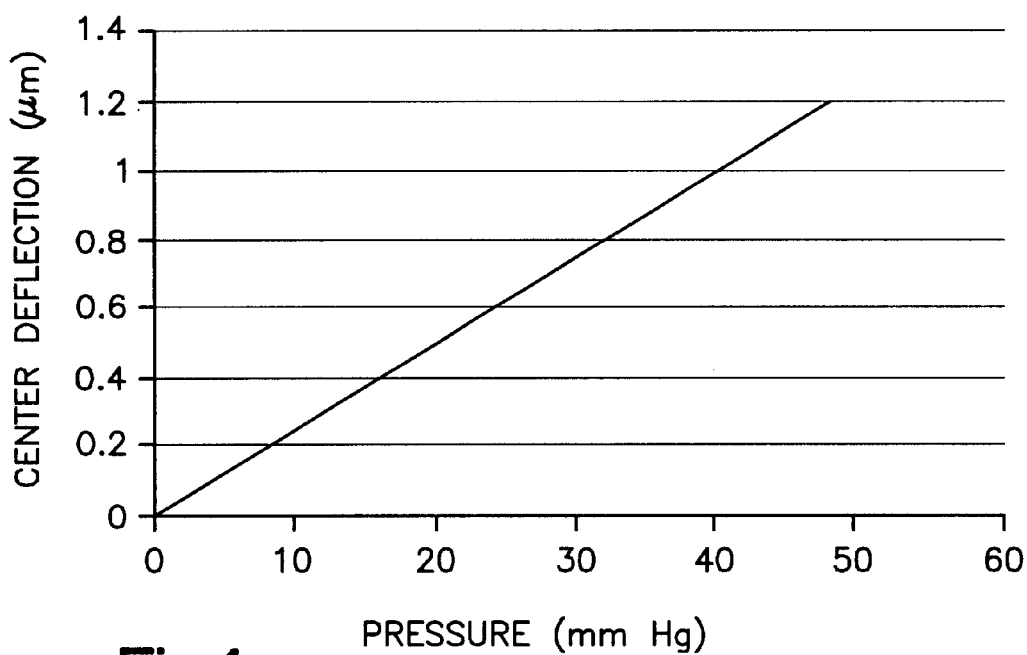
FIG. 4 is an exemplary graph illustrating the connection between the diaphragm deflection of a MEM tonometer sensor embodiment and intraocular pressure (IOP).
Figure 5:
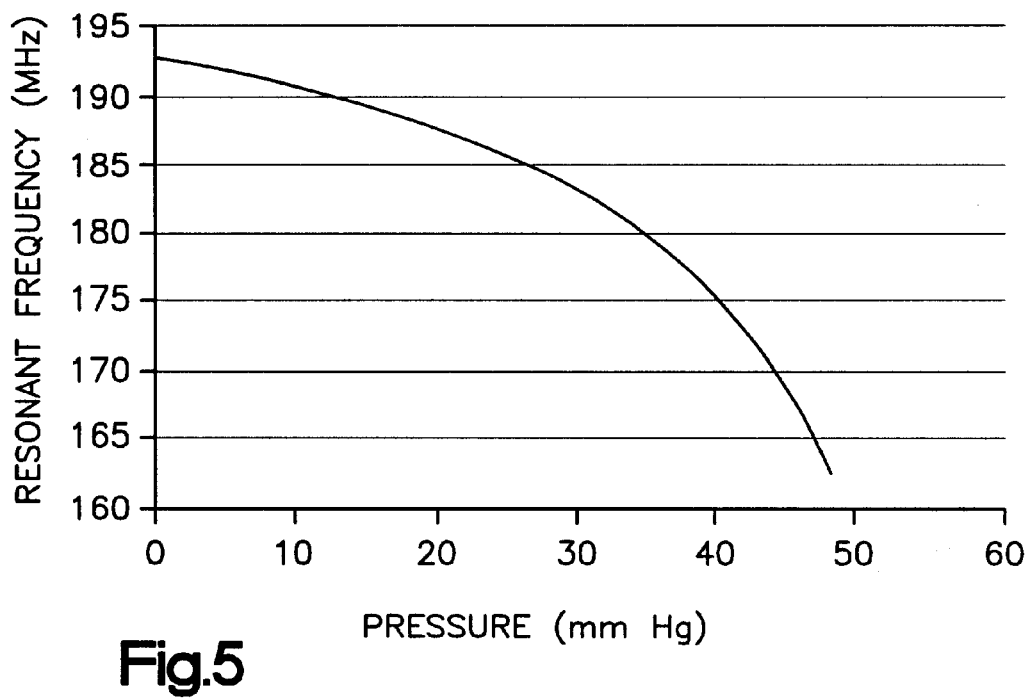
FIG. 5 is an exemplary graph illustrating the connection between resonant frequency of the MEM tonometer sensor embodiment and IOP.

As has been described in connection with the illustration of FIG. 3A, the deflection of the diaphragm of the compliant region 18 as the contact surface 14 of the substrate 12 is pressed against the surface portion 34 of the eye 36 is representative of the IOP of the eye The graph of FIG. 4 illustrates an exemplary center deflection in micrometers ($\mu$m) expected for a diaphragm with the geometry described above as a function of the IOP of the eye expressed in parametric units of millimeters of Mercury (mm of Hg). It is this deflection of the diaphragm which causes the change in capacitance and may be measured by the resultant change in resonant frequency of the tank circuit. The graph of FIG. 5 illustrates an estimated change in resonant frequency based upon a conservative approximation of a corresponding change in capacitance resulting from the diaphragm's deflection or IOP. The expression of resonant frequency (MHz) to IOP (mm Hg) illustrated by the graph is non-linear as expected in a capacitve sensing structure for measuring IOP.

Figure 6:
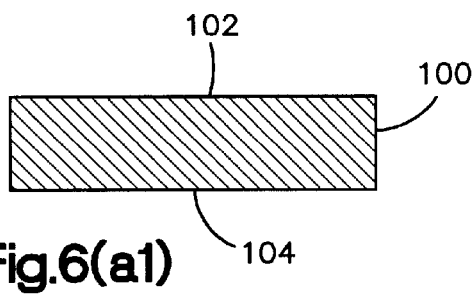
FIGS. 6(a)–6(i) are cross-sectional and plan views of the MEM tonometer sensor embodiment through various stages of a fabrication process.
Figure 6:
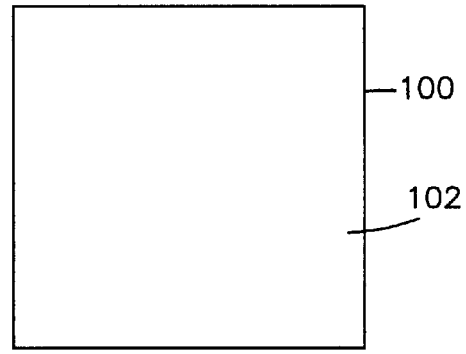
Figure 6:
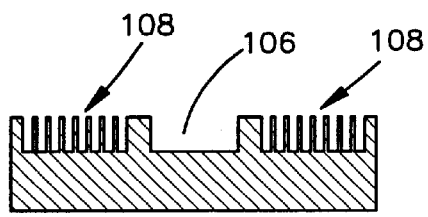
Figure 6:
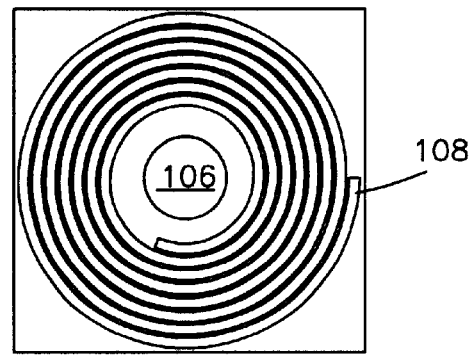
Figure 6:
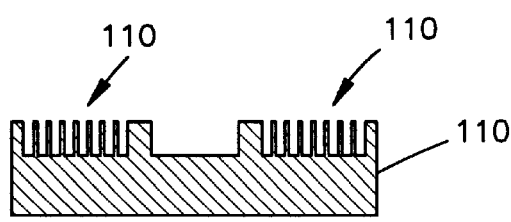
Figure 6:
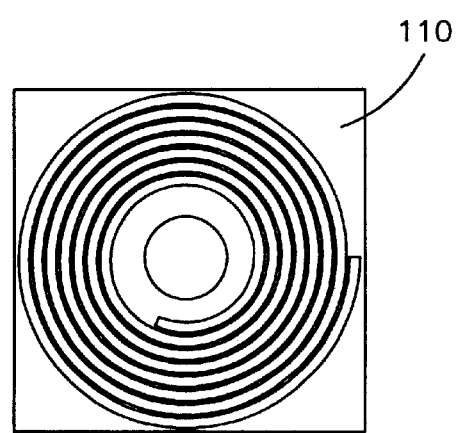
Figure 6:
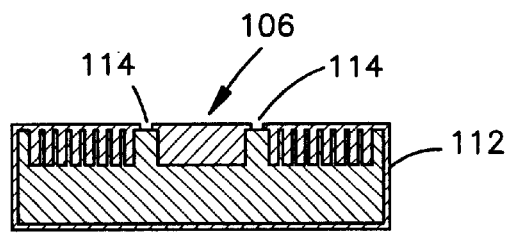
Figure 6:
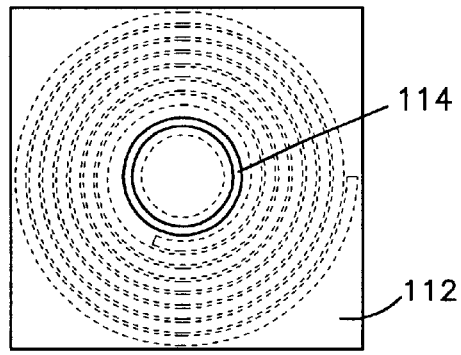
Figure 6:
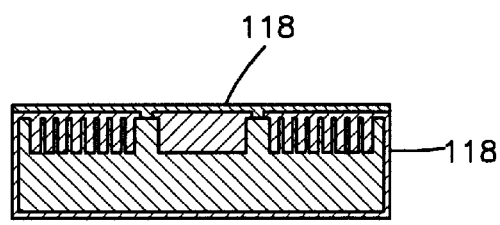
Figure 6:
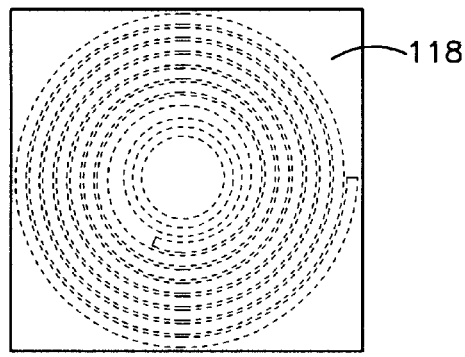
Figure 6:
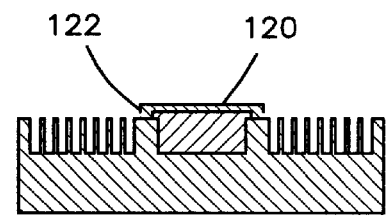
Figure 6:
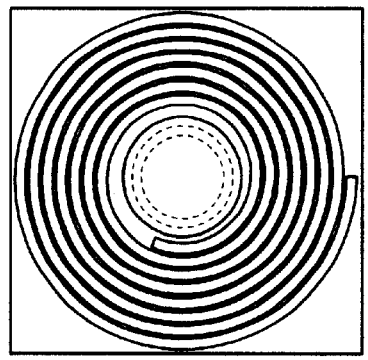
Figure 6:
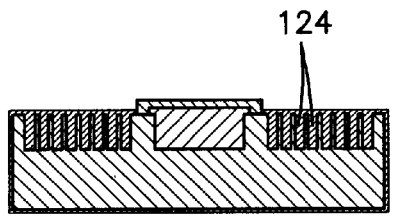
Figure 6:
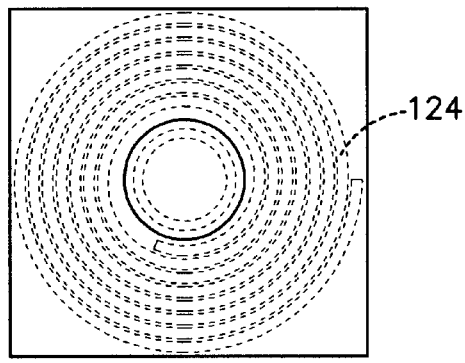
Figure 6:
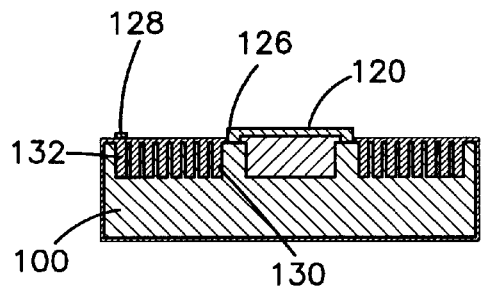
Figure 6:
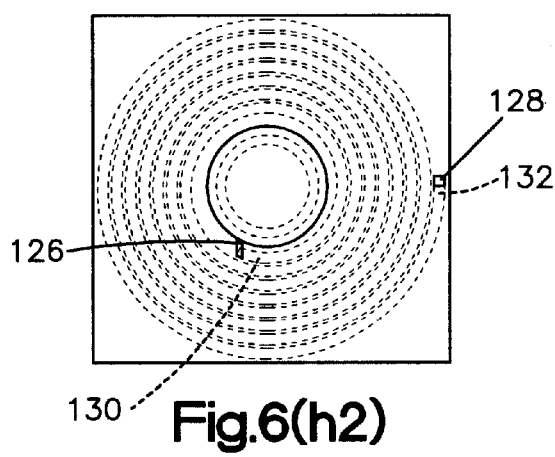
Figure 6:
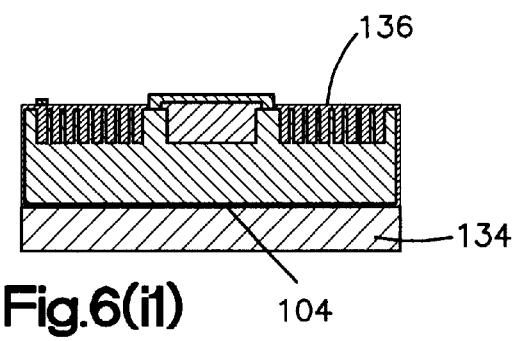
Figure 6:
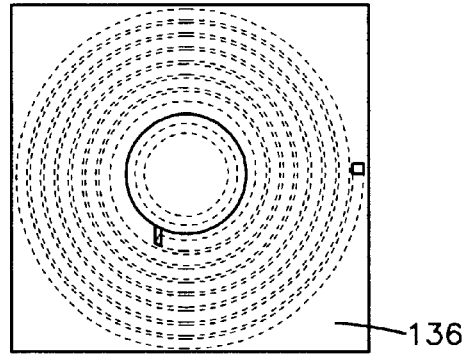

An exemplary process suitable for fabricating an embodiment of the tonometer sensor 10 is shown in the process diagrams of FIGS. 6(a) through 6(i) wherein each figure provides for cross-sectional and top or plan views of the sensor structure at various stages of the fabrication process. The process starts with a substrate 100 which may be part of a Silicon wafer, for example, as shown in FIG. 6(a). It is understood that materials other than Silicon may be used for the substrate in which case the process may be slightly modified to accommodate such other material. The substrate has a top surface 102 and a bottom surface 104. In the step of FIG. 6(b), an etch resist layer is provided over the substrate, like Silicon Dioxide ($SiO_2$), for example, and the top surface 102 is patterned using conventional lithography/etching processes to form the capacitor well region 106 having a diameter of approximately 500 µm, for example, (but another diameter may work just as well) and spiraled groove regions 108 of a width on the order of 5 µm, for example, for the inductor coil. Thereafter, the unpatterned etch resist areas of the Si substrate are etched using a deep etch process, like reactive ion etching, for example, to a depth of one to twenty microns and the etch resist is removed rendering a structure as shown in FIG. 6(b).

In the step of FIG. 6(c), a layer of Silicon Nitride ($Si_3N_4$) or other similar material 110 is deposited on the surfaces of the substrate 100. In the present embodiment, a conformal coating of $Si_3N_4$ is deposited over the surface of the substrate through a conventional chemical vapor deposition (CVD) process to a thickness of approximately 1200 Å–2400 Å, for example, but another thickness may work just as well. Next, in the step of FIG. 6(d), a layer of low temperature oxide (LTO) 112 is deposited over the $Si_3N_4$ layer 110 by conventional CVD to a thickness of approximately 2–3 82 m, for example. The LTO layer 112 of the top surface 102 is polished smooth using a chemical mechanical polishing process, for example, and patterned using a conventional photolithography process to form an anchor region 114 which for the present embodiment is in the form of an annulus of a width of approximately 50–100 microns surrounding the capacitive well region 106. The anchor region 114 is etched through the LTO down to the $Si_3N_4$ layer using a reactive ion etching process, or a wet etching process using buffered hydrofluoric acid (BHF), for example, or other similar process. In the step of FIG. 6(e), a layer of polysilicon 118 is deposited, preferably by CVD, over the surface of the LTO layer of FIG. 6(d) and the layer of polysilicon at the top surface is patterned and etched in a conventional manner to form an unetched layer of polysilicon 120 covering substantially the capacitive well region 106 and anchored by region 114 to the nitride layer. A hole 122 may be provided through an edge of the polysilicon layer 120 to the LTO and $Si_3N_4$ layers thereunder by the aforementioned patterning and etching process of FIG. 6(e). A post annealing process is performed to render the membrane section of polysilicon 120 in tension. In the present embodiment, the structure of FIG. 6(f) is put in an oven and heated for approximately 30 minutes at approximately 900° C. which changes the crystalline makeup of the polysilicon to provide for stress modification thereof.

In the step of FIG. 6(f), the LTO and Nitride layers, including the layers under the polysilicon layer 120, are removed, preferably by a conventional BHF etching process wherein the BHF is allowed to flow through the hole 122 and etch the LTO and Nitride layers under the polysilicon layer 120 which are released in solution through the same hole 122. Accordingly, a polysilicon diaphragm 120 in tension is produced as shown in FIG. 6(f). Next, the hole 122 in the polysilicon diaphragm is sealed by growing a low temperature oxide layer (not shown) over the hole 122 in a conventional furnace environment. In the step of FIG. 6(g), the grooved areas 108 may be pre-treated to accept a conductive material which may be deposited in the grooves by conventional plating, sputtering or evaporation techniques, for example, to form the inductor coil 124. Metals which may be used for this process may be Ni, Au, Fe, Ag, and Pt to name just a few. Preferably, the metallic plating is performed electroless, but electroplating may also be used without deviating from the principles of the present invention.

As shown in FIG. 6(h), interconnects 126 and 128 are provided from the ends of the the inductor coil 124 to corresponding sides of the capacitive element. For the interconnect region 126, a window is formed in the Nitride layer between the conductive material of the inside coil 130 and the polysilicon layer 120 which is one side of the capacitive element of the sensor. When the window region is plated, the metal end 130 of the inductor coil will make electrical contact with one side 120 of the capacitive element. For the interconnect region 128, a window is formed in the Nitride layer between the substrate and the groove of the other end 132 of the coil such that when plated, metal electrically connects the other end 132 of the coil with the silicon substrate 100 which is the other side of the capacitive element thus, completing the tank or oscillatory circuit. In the step of FIG. (i), the material 134 of the permanent magnet may be provided to the bottom surface 104 of the substrate using any one of the well known processes, such as plating, bonding or even silk screening, for example, to form a permanent magnet layer 134. Still further, a thin layer of non-conducting material 136 may be grown over the metallic plated surfaces of the non-compliant region to ensure against the sections of coil 124 making contact with each other over the surface of the Nitride layer.

Figure 7:
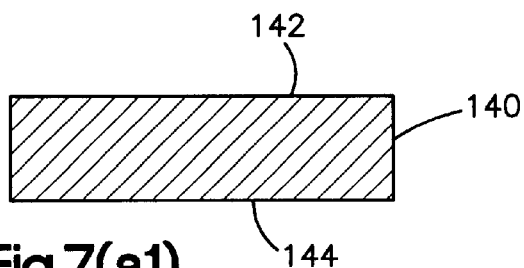
FIGS. 7(a)–7(j) are cross-sectional and plan views of an alternate MEM sensor embodiment through various stages of a fabrication process.
Figure 7:
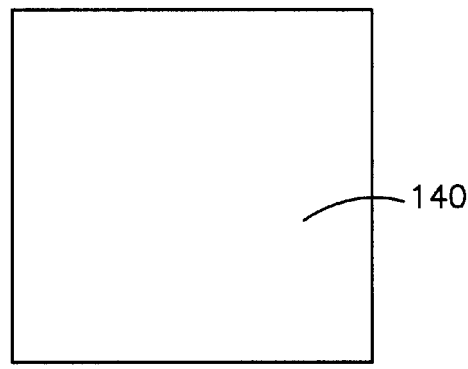
Figure 7:
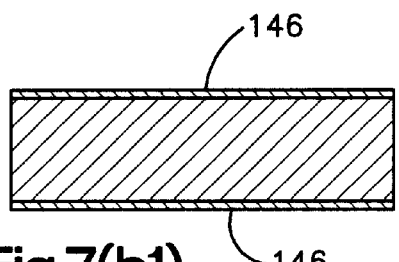
Figure 7:
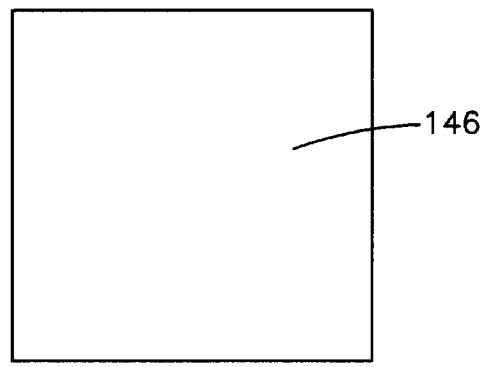
Figure 7:
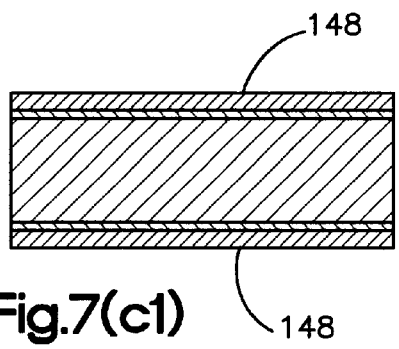
Figure 7:
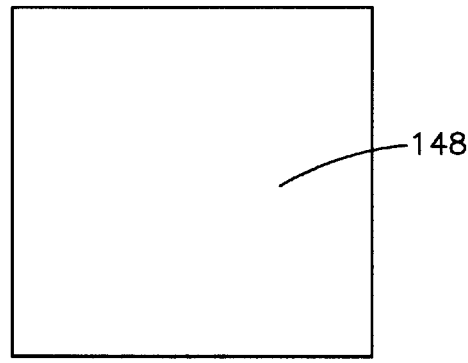
Figure 7:
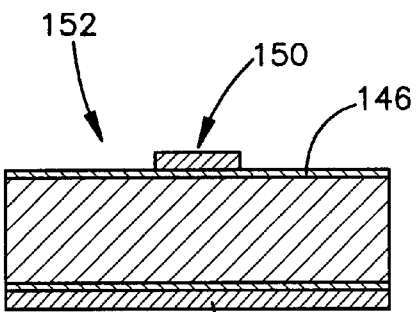
Figure 7:
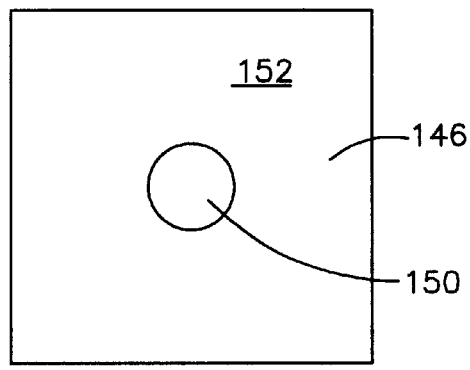
Figure 7:
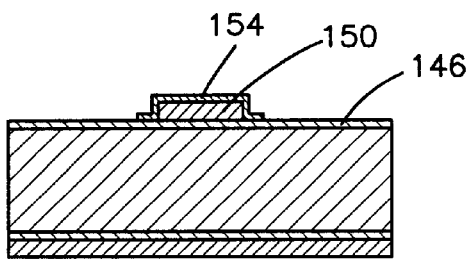
Figure 7:
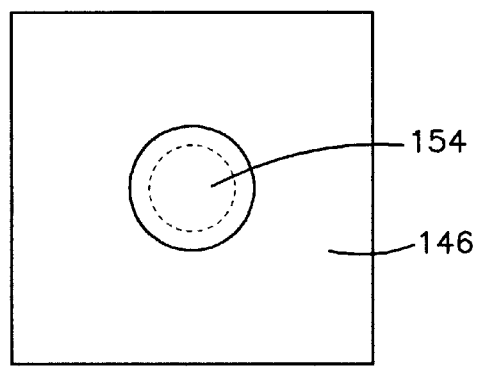
Figure 7:
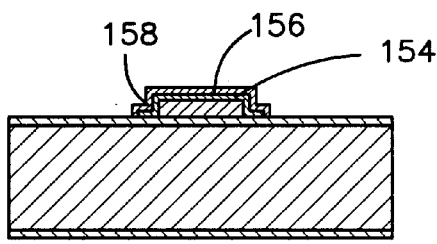
Figure 7:
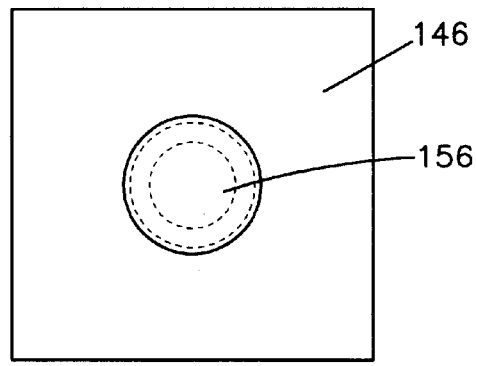
Figure 7:
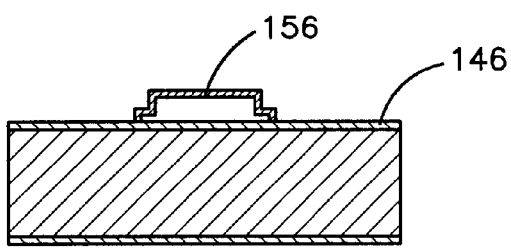
Figure 7:
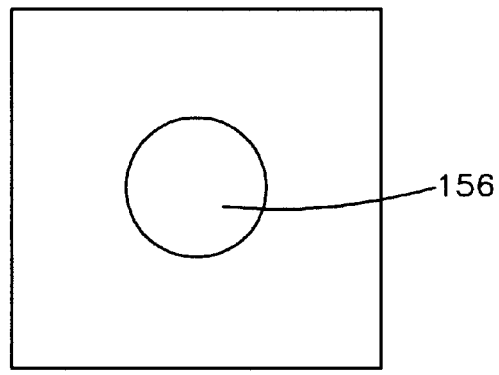
Figure 7:
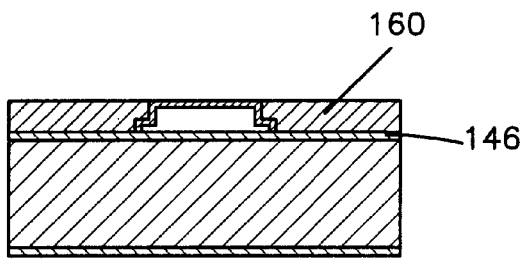
Figure 7:
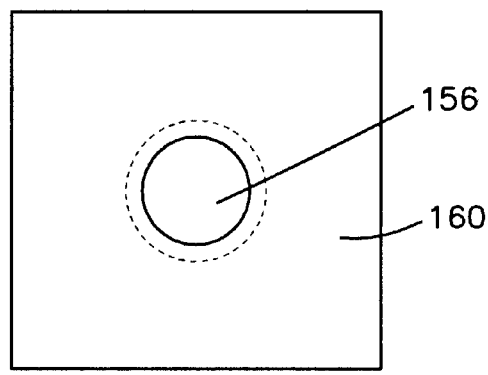
Figure 7:
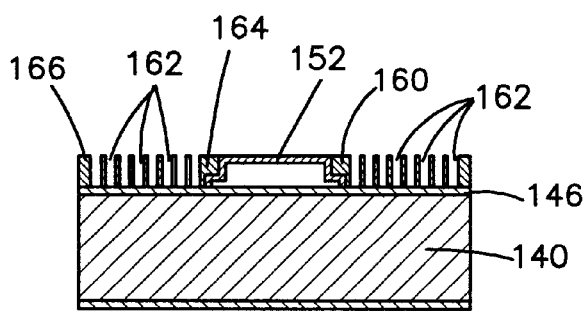
Figure 7:
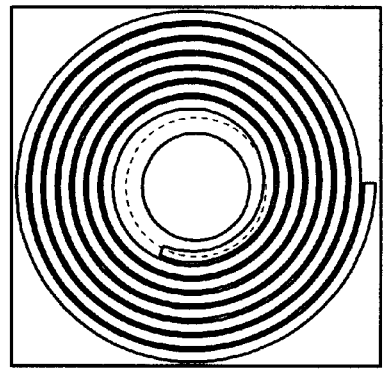
Figure 7:
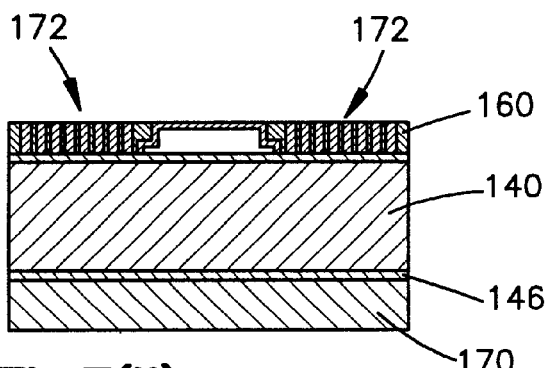
Figure 7:
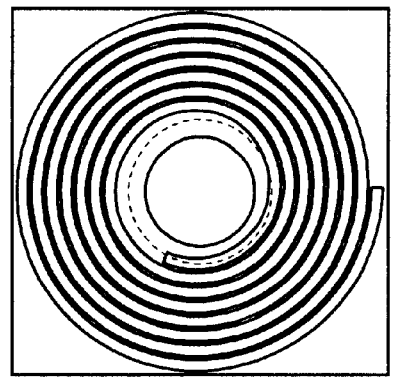

An exemplary embodiment for illustrating a fabrication process of an alternate embodiment of the tonometer sensor 10 is shown in the FIGS. 7(a) through 7(j) wherein each figure provides for cross-sectional and top or plan views of the alternate sensor structure at various stages of the fabrication process The process starts with a substrate 140 which may be part of a Silicon wafer, for example, as shown in FIG. 7(a). It is understood that materials other than Silicon may be used as for the substrate in which case the process may be slightly modified to accommodate such other material. The substrate 140 has a top surface 142 and a bottom surface 144. In the step of FIG. 7(b), a layer of Silicon Nitride ($Si_3N_4$) or other similar material 146 is deposited on the top and bottom surfaces of the substrate 140. In the present embodiment, the $Si_3N_4$ is deposited through a conventional chemical vapor deposition (CVD) process to a thickness of approximately 1200 Å, for example, but another thickness may work just as well. Next, in the step of FIG. 7(c), a layer of low temperature oxide (LTO) 148 is deposited over the $Si_3N_4$ layer 146 by conventional CVD to a thickness of approximately 1.5 µm, for example. The LTO layer 148 of the top surface 142 is patterned using a conventional photolithography process to form a circled region 150 having a diameter of approximately 500 µm, for example, (but another diameter may work just as well) on top of the $Si_3N_4$ layer 146 and the unpatterned regions 152 around the circled region 150 and on the bottom surface 144 are etched using a reactive ion etching process, or a wet etching process using buffered hydrofluoric acid (BHF), for example, or other similar process.

The top surface 142 of the resulting structure as shown in FIG. 7(d) is deposited with another low temperature oxide layer, preferably by CVD, to a thickness of approximately 0.5 µm, for example. This second LTO layer is patterned and etched in a conventional manner such that the remaining unetched second LTO layer 154 overlaps the circled layer 150 concentrically to form an annular region of approximately 50 µm on top of the $Si_3N_4$ layer 146 surrounding the circled region 150 as shown in FIG. 7(e). In the step of FIG. 7(f), a layer of polysilicon is deposited, preferably by CVD, over the top surface of the structure of FIG. 7(e) and the layer of polysilicon is patterned and etched in a conventional manner to form an unetched layer of polysilicon 156 covering substantially the second LTO layer 154. A hole 158 may be provided through the polysilicon layer 156 to the LTO layers 150 154 thereunder by the aforementioned patterning and etching process of FIG. 7(f). A post annealing process is performed to render the membrane section of polysilicon 156 in tension. In the present embodiment, the structure of FIG. 7(f) is put in an oven and heated for approximately 30 minutes at approximately 900° C. which changes the crystalline makeup of the polysilicon to provide for stress modification thereof.

In the step of FIG. 7(g), the LTO layers 150 and 154 under the polysilicon layer 156 are removed, preferably by a conventional BHF etching process wherein the BHF is allowed to flow through the hole 158 and etch the LTO layers under the polysilicon layer 156 which are released in solution through the same hole 158. According, a polysilicon diaphragm 156 in tension is produced. Next, the hole 158 in the polysilicon diaphragm is sealed by growing a low temperature oxide layer over the hole in a conventional furnace environment. Next, in the step of FIG. 7(h), a polymer layer 160 which may be a photosensitive polyimide, a photoresist material, PMMA, or the like, is deposited over the $Si_3N_4$ layer 146 of the top surface. Patterning of the polymer layer depends on the type of polymer used. For example, if a polyimide is used, conventional photolithography may be used to form the annular winding pattern of the inductor coil. The patterned portions of the polyimide are etched conventionally down to the $Si_3N_4$ layer 146 to provide grooves 162 in which to plate the metallic material of the inductor coil within the polyimide layer 160 on the $Si_3N_4$ layer as shown in FIG. 7(i). Preferably, the metallic plating is performed electroless, but electroplating may also be used without deviating from the principles of the present invention. One groove 164 in the polyimide layer 160 goes down to the annulus of the polysilicon layer 156 so that when plated, the metal end of the inductor coil will make contact with the polysilicon 156 which is one side of the capacitive element of the sensor. In addition, a hole may be provided through the $Si_3N_4$ layer at the groove 166 of the other end of the coil to allow the plated metal in the groove 166 to pass through the hole and make contact with the Silicon substrate 140 which is the other side of the capacitive element thus, completing the tank or oscillatory circuit. The material of the permanent magnet may be plated to the $Si_3N_4$ surface 146 on the bottom of the substrate to form a permanent magnet layer 170 as shown in FIG. 7(j). The layer 170 may also be formed by bonding a layer of permanent magnet material to the $Si_3N_4$ layer 146 using conventional bonding techniques. Still further, a thin layer of non-conducting material may be grown over the metallic plated surfaces 172 of the non-compliant region to ensure against the sections of coil making contact with each other over the surface of the polyimide layer 160.

While the present MEM sensor embodiment is described as being fabricated on a Silicon substrate, it is understood that other substrates may be used such as plastic and polymer films, for example. Such an alternate MEM sensor could also be fabricated using a well-known micro-replication process in which a thin film of plastic or polymer is mechanically patterned, preferably with dimples that would represent wells, by any conventional process. The film would then be metalized to form a ground electrode. A second film could be metalized in a pattern to form an inductor and capacitor (tank circuit). The two films may then be aligned and bonded together to produce a tonometer sensor structure similar to the structures described herein above for a Silicon substrate, but made from a plastic or polymer film instead.

Figure 8:
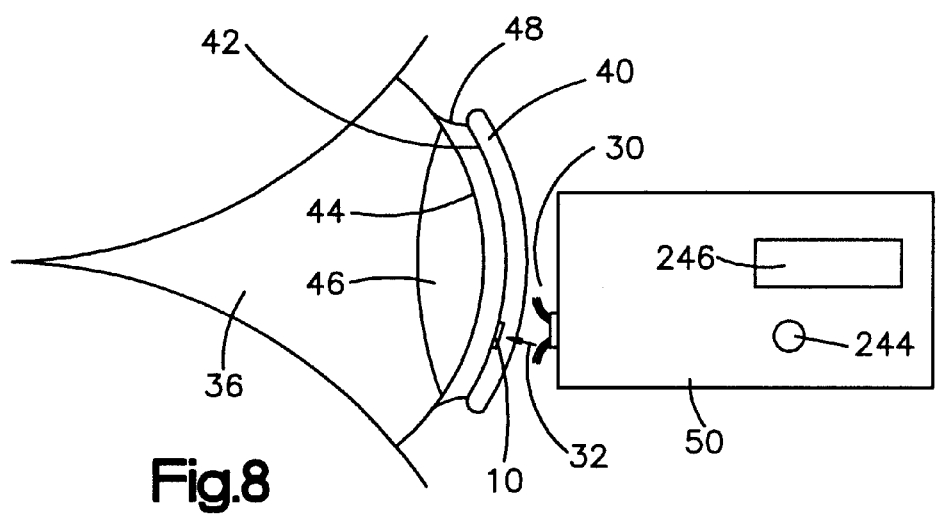
FIG. 8 is an illustration of a tonometer system utilizing a flexible contact lens with a MEM tonometer sensor at a surface thereof suitable for embodying another aspect of the present invention.
Figure 9:
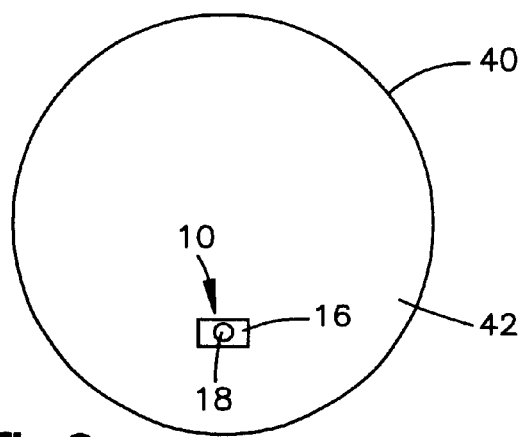
FIG. 9 is an illustration of a flexible contact lens with a MEM tonometer sensor at a surface thereof suitable for embodying another aspect of the present invention.

An embodiment of a tonometer system utilizing the tonometer sensor 10 is illustrated in FIG. 8. Referring to FIG. 8, a flexible contact lens 40 which may be made of hydrogel, for example, is disposed in proximity to a portion of the eye 36. A surface 42 of the lens 40 is contoured to the surface portion 44 of the eye 36 which may be the area of the cornea 46, for example. The lens 40 may rest on a teary liquid 48 which normally covers the surface 44 of the eye. The tonometer sensor 10 is disposed at the surface 42 of the lens 40 such that the contact surface 14 thereof faces a portion of the eye surface 44. The illustration of FIG. 9 of the contact lens 40 reveals the sensor 10 mounted off center at the surface 42 thereof. FIG. 9 shows the non-compliant and compliant regions 16 and 18, respectively, facing outward from lens surface 42 in order to make contact with the cornea surface of the eye when forced to do so. In the present embodiment, the sensor 10 will provide some weighting to the lens when mounted thereto. Therefore, when the lens is positioned in proximity to the eye and floats on the surface liquid thereof, the sensor will be oriented at the lower part of the lens due to the force of gravity. This permits a preferred or fixed orientation of the sensor for alignment purposes as will be better understood from the description below.

The sensor 10 may be incorporated into the lens, preferably at the lens surface 42, during the lens fabrication process, for example. For example, if the lens is made using a spin casting process, the lens solution is injected onto a spinning mold, the spin rate and time being typically computer controlled. The MEM tonometer sensor 10 may be placed in a pocket machined into the mold and held in place via vacuum, for example. When the molding is complete, the vacuum is removed from the sensor 10, the contact lens is removed from the mold and the lens with the incorporated sensor is handled using conventional procedures. Accordingly, the flexible contact lens including the tonometer sensor may be a separate article of manufacture in accordance with one aspect of the present invention.

Figure 10:
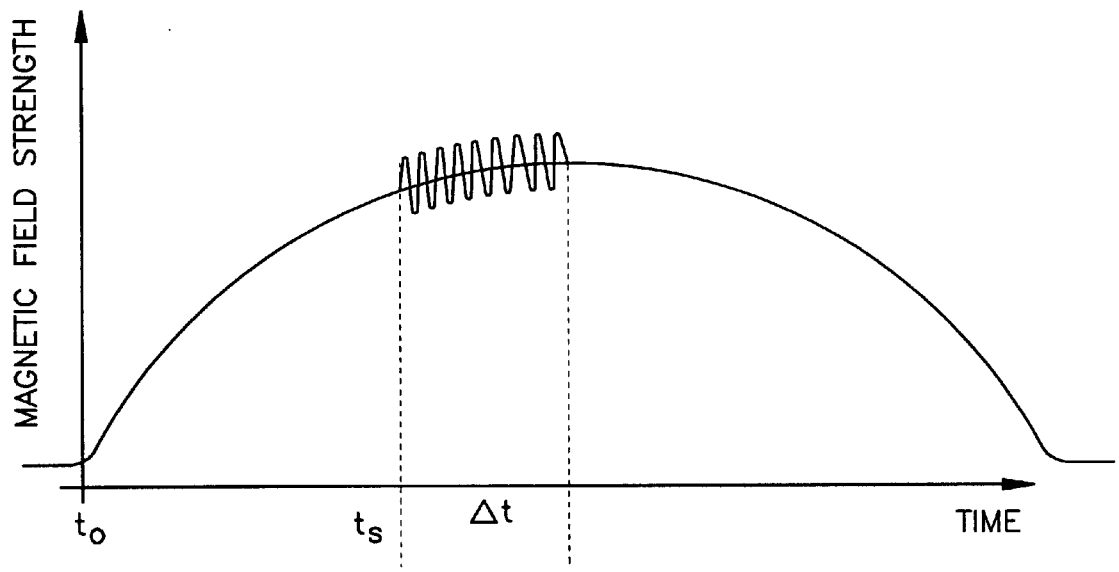
FIG. 10 is a time graph exemplifying a magnetic field strength vs. time envelope produced by the tonometer system embodiment of FIG. 8.

Referring back to FIG. 8, a control unit 50 positionable in proximity to the contact lens 40 and aligned in the vicinity of the sensor 10 generates, upon activation, a non-invasive force signal which may be the magnetic field 30, for example, over a predetermined time interval to create the repulsive force 32 which presses the contact surface 14 of the sensor 10 against the surface portion of the eye which for the present embodiment is in the area of the cornea 46. The strength of the magnetic field 30 may be varied by the control unit 50 over the predetermined time interval to cause the contact surface of the sensor 10 to be pressed against and then, released from the surface portion of the eye with a respective varying force. FIG. 10 is a time graph exemplifying the magnetic field strength envelop in time over an interval spanning one to two seconds, for example.

The response of the lens 40 and tonometer sensor 10 to the increasing strength of the magnetic field over time is shown in the exemplary illustrations of FIGS. 11A through 11E. Each of the FIGS. 11A through 11E provide an illustration of the position of the sensor 10 in relation to the eye 36 and a corresponding time graph of a pressure representative signal vs. time. The darkened or highlight ed region along each time graph is the time interval represented by the respective illustration. In FIG. 11A, the magnetic repulsive force 32 initially advances the sensor 10 toward the cornea surface of the eye 36 causing the lens to flex under the force. In FIG. 11B, the compliant region 18 of the sensor 10 initially meets the surface of the eye 36. The initial dip in pressure at 60 from the base line pressure 62 may be due to surface tension attracting the diaphragm of the compliant region 18 just before actual contact with the eye surface.

Accordingly, as the sensor is pressed further against the eye surface and the diaphragm is depressed as shown in FIG. 11C, the pressure representative signal will continue to increase. As the flattening of the eye surface increases, the sense d pressure peaks as shown at point 64 in FIG. 11D and starts to decrease as a result of the bending forces of the cornea being transferred from the compliant region 18 to across the non-compliant region 16 of the sensor 10. Point 64 represents the initial crest of the pressure representative signal. As the sensor 10 is pressed further against the eye surface as shown by the illustration of FIG. 11E, the pressure reaches a minimum at point 66 and this minimum represents the IOP of the eye. Thereafter, as the magnetic field strength continues to increase and force the sensor against the eye surface, the pressure increases beyond the IOP stage due primarily to an artificial elevation of IOP resulting from additional applanation and other forces in the eye like, surface tens ion of tearing shown at 68, bending force shown at 70, and tissue tension shown at 72, for example. After the IOP has been measured via sensor 10, the magnetic field strength may be decreased as shown by the profile of the time graph of FIG. 10 until the sensor and lens are returned back to their original positions and the pressure reading is baselined at level 62. The lens 40 and sensor 10 included therein are then ready for the next IOP measurement.

In order to take IOP measurements non-invasively from the sensor 10, the control unit 50 may also generate the activation signal for energizing the impedance element of the sensor 10 to measure a signal representative of the IOP. This activation signal may be an electromagnetic signal that varies over a predetermined radio frequency range say from one hundred to two hundred megahertz (100–200 MHz), for example, that energizes the tank circuit of the sensor 10 and causes it to resonate. The control unit 50 may also include a circuit to detect the resonant frequency of the sensor's tank circuit which is proportional to the IOP as shown by the graph of FIG. 5, for example. This activation signal may be transmitted from the control unit 50 multiple times over the predetermined time interval during which the magnetic field is being applied to take sampled data points of the pressure so that the minimum pressure representative of the actual IOP may be determined (refer to FIG. 11E).

Figure 10A:
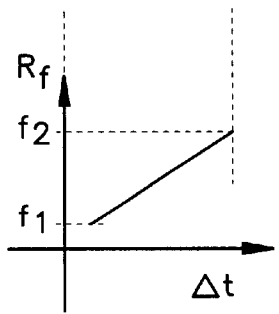
FIG. 10A is a graph exemplifying the frequency sweep of the activation signal over a time interval produced by the tonometer system embodiment of FIG. 8.

In one embodiment, the electromagnetic activation signal is superimposed on the magnetic field signal as shown by the graph of FIG. 10. For each interval $\Delta t$ which is much smaller than the predetermined time interval over which the magnetic field is being applied, the electromagnetic signal is ramped from a starting frequency $f_1$ to an ending frequency $f_2$ as illustrated in the graph of FIG. 10A. The range of all possible resonant frequencies representative of measured IOPs during the application of the magnetic field will fall within the frequency range of the graph of FIG. 10A. Accordingly, for each interval $\Delta t$, a resonant frequency is determined which is representative of a pressure measurement sampling point during the application of the magnetic field and the collection of these pressure measurement data or sampling points provide for a pressure vs. time graph as exemplified by FIG. 11E in order to determine the minimum or actual IOP.

Figure 12:
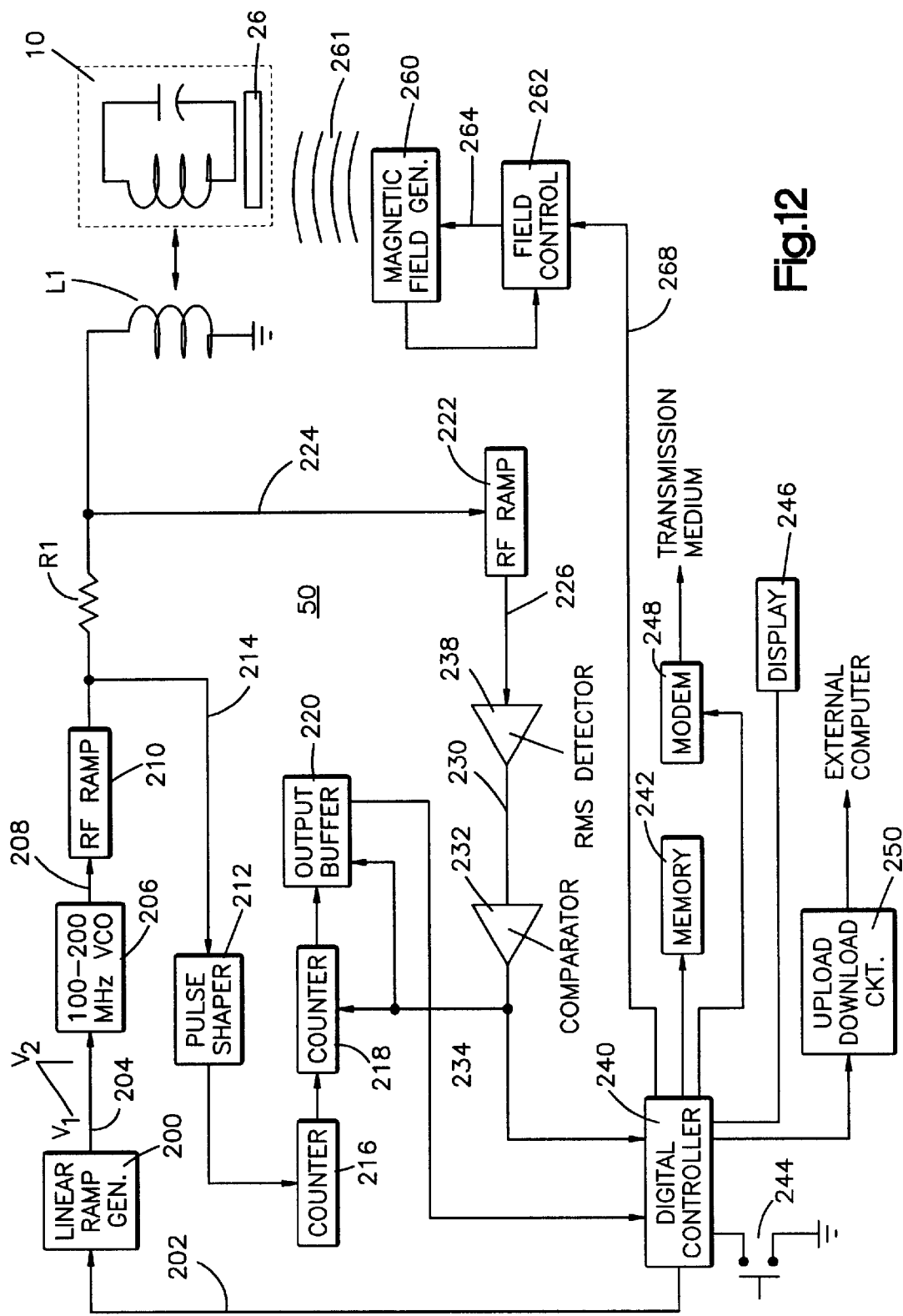
FIG. 12 is a functional block diagram schematic of a control unit suitable for use in the system embodiment of FIG. 8.

A block diagram schematic of the control unit 50, which may be portable, for example, suitable for embodying the principles of the present invention is shown in FIG. 12. Referring to FIG. 12, a circuit 200 may be triggered by a signal 202 to generate a linear ramping signal 204 which ranges from voltages V1 to V2 over a predetermined time interval $\Delta t$, say on the order of 1 millisecond, for example. At the end of the time interval $\Delta t$, the voltage returns to a predetermined voltage setting to wait for the next trigger signal over line 202. The linear ramping signal 204 governs a voltage controlled oscillator (VCO) circuit 206 to generate a sinusoidal signal 208 which ranges in frequency from 100 MHz to 200 MHz, for example, as signal 204 ramps from V1 to V2. The signal 208 may be amplified by a radio frequency (RF) amplifier circuit 210 which drives a resister/inductor series combination, R1 and L1, respectively. The output of the RF amplifier 210 may be provided to a pulse shaper circuit 212 over signal line 214 which in turn is coupled to a cascaded pair of digital counters 216 and 218. The digital output of counter 218 may be captured in an output buffer 220.

In the present embodiment, the voltage across the inductor L1 is input to another RF amplifier 222 via signal line 224. The output 226 of the RF amplifier 222 is provided to a root-mean-square (RMS) detector 228, the output 230 of which being coupled to a comparator circuit 232. In the present embodiment, the comparator circuit 232 functions as a signal peak or valley detector and generates a signal over line 234 when the signal peak or valley is detected. The signal line 234 is coupled to the counter 218 and output buffer 220 for operation thereof. The circuits of the control unit 50 may be centrally controlled in operation by a digital controller 240, which may be a programmed microprocessor, digital signal processor or a combination of hardwired digital logic circuits, for example. A memory unit 242 is coupled to the digital controller 240 and may be comprised of a combination of static, dynamic and read-only memory units, for example, for the storage of data and program information. A switch 244 which may be of the push-button variety, for example, is coupled to the digital controller 240 through conventional input-output circuitry (not shown). The digital controller may also be coupled to a conventional display unit 246 for displaying IOP readings and a modem 248 which may transmit data between the control unit 50 and a remotely located unit over the telephone lines or a wireless service, for example. The control unit 50 may also include an upload/download circuit 250 for transmitting data between the controller 240 and an external computer, like a PC, for example, over a hardwired connection.

Also, the control unit 50 includes a magnetic field generation unit 260 which may be a conventional coil circuit for generating a magnetic field 261 electromagnetically, for example. A magnetic field control circuit 262 may be further included to control the magnetic field strength according to the time curve of FIG. 10 by adjusting a current signal 264 applied to the field generator 260, for example. A feedback signal 266 may be supplied from the field generator 260 to the control unit 262 to provide for an more accurate magnetic field strength vs. time profile generation. An initiation signal is provided from the digital controller 240 to the field control unit 262 over signal line 268. In an alternate embodiment, the activation signal from the RF amplifier 210 may be capacitively coupled to the field control circuit 262 for superimposing the activation signal on the magnetic field signal as shown in the profile of FIG. 10. In a further embodiment, the circuit may be modified such that the magnetic field strength is controlled through the RF amplifier by varying the DC bias thereto in accordance with proposed profile, for example.

Taking an IOP reading using the control unit 50 in combination with a flexible contact lens 40 having the sensor 10 incorporated therein will now be described in connection with the FIGS. 8, 9, 10, 10A, 11E and 12. A course alignment of the control unit 50 with the lens/sensor combination, as illustrated in FIG. 8, may be manually self-controlled by the individual performing the IOP measurement. Weighting the lens 40 to provide for the sensor 10 to be at a preferred orientation to the pupil of the eye may improve alignment. This technique is conventionally practiced in the contact lens industry to provide a lens prism orientation for the correction of astigmatism. The handheld control unit 50 may also be aligned with the lens/sensor unit through use of a mold that is part of the unit 50 and shaped to fit over the eye socket. It is understood that there are a variety of ways in which the portable control unit 50 may be aligned with the lens/sensor combination, any one of which being suitable for the practice of the present invention. Once the portable control unit 50 is brought in close proximity to the lens/sensor combination as shown in FIG. 8, the pushbutton 244 may be depressed for taking an IOP reading. In response to the depression of the pushbutton 244, the digital controller 240 autonomously commences with a sequence of control operations to perform the IOP reading.

Initially, the digital controller 240 signals the magnetic field control circuitry 262 over signal line 268 to commence the magnetic field profile as shown in FIG. 10. In the present embodiment, the permanent magnet region 26 of the sensor 10 is repelled by the magnetic field 261 which noninvasively forces the sensor 10 against the surface of the eye. After a brief time delay and as the magnetic field strength is increasing, trigger signals are generated at predetermined times over signal line 202 to cause the linear ramp circuit 200 to generate the ramping signals which controls the VCO to drive the inductor L1 via RF amplifier 210 and resister R1. In turn, the inductor L1 is coupled magnetically to the inductor of the sensor 10 and electromagnetically activates and drives the tank circuit of the sensor 10. As has been described herein above, the capacitive element (compliant region)of the sensor 10 will change in impedance as it is forced against the surface of the eye. This change in impedance will cause a change in circuit resonance. Sensor readings are thus taken at the points of resonance of the magnetically coupled circuits. More specifically, during the time interval of each frequency ramp, the RMS voltage across the inductor L1 is monitored by the circuits 222, 228 and 232 to establish the point in time of resonance. At resonance, a signal is generated by the comparator circuit 232 to the controller 240, counter 218 and output buffer 220. In response to this signal, the digital count of counter 218 which is representative of the resonance frequency is captured in the output buffer 220 and subsequently, read by the controller 240 and stored in the memory 242. The stored digital counts of each of the frequency sweep time intervals represent sampled data points which together form the pressure profile described in connection with FIG. 11E. The digital controller 240 processes these sampled data points to determine the current IOP reading which may be day and time stamped and stored in the memory 242 and displayed in the digital display 246. The magnetic field is reduced in accordance with the profile of FIG. 10.

Accordingly, IOP readings may be conveniently taken and stored in the control unit 50 at multiple times during the period of a day by a patient for a period of days and weeks. In addition, the portable control unit 50 may be linked to a remote site, like a doctor's office, hospital and the like, for example, via the modem 248 through a transmission medium to communicate the IOP readings and their date/time stored in the memory 242 as controlled through the controller 240. Command signals for performing this operation may initiate from the remote site via the modem 248. In addition, the portable control unit 50, which may be hand held, for example, may be carried with the patient to the remote site and the IOP readings and their date/time stamps uploaded to a digital computer at the remote site using a hardwired connection to the circuit 250. A doctor may thus monitor a patient's IOP readings over a period of days or weeks with multiple readings taken per day to more accurately diagnose a degenerative eye condition.

The control unit 50 may be also used as part of an instrument in a doctor's office. Currently, some doctor's use a Goldman applanation tonometer which is an optical piece of equipment where the operator looks through a prism and aligns marks superimposed on the eye to determine IOP. Sterilization causes difficulty in verifying the efficacy of the Goldman IOP readings. Goldman tonometers are not conveniently sterilized in soaking solutions or an autoclave. Rather, they are sterilized by wiping with an alcohol pad between uses. The control unit 50 may be outfitted onto a slit lamp in place of the Goldman tonometer. In such an implementation, the applanation pressure could be controlled in the same manner as for the Goldman tonometer using a dial and lever and the IOP information would be provided electronically via an upload circuit and a display. The clinician would no longer have to optically align prisms and their would be no need for sterilization with the use of disposable contact lens/sensor units.

While the present invention has been described herein above in connection with a plurality of embodiments, it is understood this description has been set forth solely by way of example and that additions, modifications and deletions may be made to such embodiments without deviating from the principles of the present invention. Accordingly, the present invention should not be construed in connection with any single embodiment, but rather construed in breadth and broad scope according to the recitation of the appended claims.

We claim:

1. A tonometer sensor for disposition in proximity to a portion of a surface of an eye, said sensor comprising:
    a substrate including:
        a contact surface for making contact with said surface portion of the eye, said contact surface including an outer non-compliant region and an inner compliant region fabricated as an impedance element that varies in impedance as said inner region changes shape;
        a first region of material responsive to a non-invasive external force to press said contact surface against said surface portion of the eye and cause said compliant region to change shape in proportion to an intraocular pressure of the eye; and
        a second region of conductive material electrically coupled to said impedance element of said compliant region and responsive to an external signal for energizing said impedance element so that said intraocular pressure may be determined.

2. The sensor of claim 1 wherein the substrate is comprised of silicon material.

3. The sensor of claim 1 wherein the compliant region comprises a diaphragm as one plate of a capacitive element, said diaphragm being separated by a dielectric region from an other plate of the capacitive element that is part of the substrate, said diaphragm flexing closer to said other plate as the contact surface is pressed against the surface portion of the eye to change the capacitance of the capacitive element in proportion to the intraocular pressure of the eye.

4. The sensor of claim 3 wherein the dielectric region comprises air.

5. The sensor of claim 3 wherein the second region of conductive material comprises an inductor coil that is electrically coupled to said capacitive element to form a resonant circuit; and wherein the external signal comprises an electromagnetic signal that varies in frequency to cause said resonant circuit to be energized and resonate at a frequency in proportion to the capacitance of the capacitive element so that the intraocular pressure may be determined.

6. The sensor of claim 5 wherein the inductor coil is fabricated in the non-compliant region.

7. The sensor of claim 5 wherein the inductor coil is formed by disposing conductive material in a predetermined pattern in the surface of the non-compliant region about the compliant region of the contact surface.

8. The sensor of claim 1 wherein the first region of material comprises a region of magnetic material responsive to the non-invasive external force comprising a magnetic field.

9. The sensor of claim 8 wherein the strength of said magnetic field determines the force at which the contact surface is pressed against the surface portion of the eye.

10. The sensor of claim 8 wherein the substrate includes a second surface opposite the contact surface; and wherein a layer of the magnetic material is disposed on said second surface such that its North-South poles are aligned substantially along an axis transverse to the contact surface of the substrate, whereby said layer of magnetic material is repelled by the external magnetic field to press the contact surface against the surface portion of the eye.

11. The sensor of claim 1 wherein the contact surface area of the substrate is approximately one square millimeter.

12. A flexible contact lens including a tonometer sensor for disposition in proximity to a portion of a surface of an eye, said lens comprising:
 a surface contoured to said surface of the eye for disposition in proximity thereto;
 a substrate disposed at said lens surface, said substrate including:
  a contact surface for making contact with said surface portion of the eye, said contact surface including an outer non-compliant region and an inner compliant region fabricated as an impedance element that varies in impedance as said inner region changes shape;
  a first region of material responsive to a non-invasive external force to press said contact surface against said surface portion of the eye and cause said compliant region to change shape in proportion to an intraocular pressure of the eye; and
  a second region of conductive material electrically coupled to said impedance element of said compliant region and responsive to an external signal for energizing said impedance element so that said intraocular pressure may be determined.

13. The lens of claim 12 wherein the lens is comprised of a hydrogel material.

14. The lens of claim 12 wherein the substrate is affixed to the surface of the lens during the lens fabrication process.

15. The lens of claim 12 wherein the substrate is comprised of silicon material.

16. The lens of claim 12 wherein the compliant region comprises a diaphragm as one plate of a capacitive element, said diaphragm being separated by a dielectric region from an other plate of the capacitive element that is part of the substrate, said diaphragm flexing closer to said other plate as the contact surface is pressed against the surface portion of the eye to change the capacitance of the capacitive element in proportion to the intraocular pressure of the eye.

17. The lens of claim 16 wherein the dielectric region comprises air.

18. The lens of claim 16 wherein the second region of conductive material comprises an inductor coil that is electrically coupled to said capacitive element to form a resonant circuit; and wherein the external signal comprises an electromagnetic signal that varies in frequency to cause said resonant circuit to be energized and resonate at a frequency in proportion to the capacitance of the capacitive element so that the intraocular pressure may be determined.

19. The lens of claim 18 wherein the inductor coil is fabricated in the non-compliant region.

20. The lens of claim 18 wherein the inductor coil is formed by disposing conductive material in a predetermined pattern in the surface of the non-compliant region about the compliant region of the contact surface.

21. The lens of claim 12 wherein the first region of material comprises a region of magnetic material responsive to the non-invasive external force comprising a magnetic field.

22. The lens of claim 21 wherein the strength of said magnetic field determines the force at which the contact surface is pressed against the surface portion of the eye.

23. The lens of claim 21 wherein the substrate includes a second surface opposite the contact surface; and wherein a layer of the magnetic material is disposed on said second surface such that its North-South poles are aligned substantially along an axis transverse to the contact surface of the substrate, whereby said layer of magnetic material is repelled by the external magnetic field to press the contact surface against the surface portion of the eye.

24. The lens of claim 12 wherein the lens is caused to flex in response to the non-invasive external force to press the contact surface against the surface portion of the eye.

25. The lens of claim 12 wherein the contact surface area of the substrate is approximately one square millimeter.

26. The lens of claim 12 wherein the surface portion of the eye comprises the cornea.

27. A tonometer system comprising:
 a flexible contact lens including a surface contoured to a portion of a surface of an eye for disposition in proximity thereto;
 a tonometer sensor including a substrate disposed at said lens surface, said substrate including:
  a contact surface for making contact with said surface portion of the eye, said contact surface including an outer non-compliant region and an inner compliant region fabricated as an impedance element that varies in impedance as said inner region changes shape;
  a first region of material responsive to a non-invasive force signal to press said contact surface against said surface portion of the eye and cause said compliant region to change shape in proportion to an intraocular pressure of the eye; and
  a second region of conductive material electrically coupled to said impedance element of said compliant region and responsive to an activation signal for energizing said impedance element; and
 a control unit positionable in proximity to said tonometer sensor for generating said non-invasive force signal over a predetermined time interval and for generating said activation signal to measure a signal representative of said intraocular pressure.

28. The tonometer system of claim 27 wherein the first region comprises a magnetic material; and wherein the control unit includes means for generating a magnetic field as the non-invasive force signal.

29. The tonometer system of claim 28 wherein the control unit includes means for varying the strength of the magnetic field over the predetermined time interval to cause the contact surface to be pressed against and then, released from the surface portion of the eye with a respective varying force.

30. The tonometer system of claim 27 wherein the activation signal is generated during the predetermined time interval.

31. The tonometer system of claim 27 wherein the control unit includes means for generating the activation signal superimposed on the non-invasive force signal.

32. The tonometer system of claim 27 wherein the compliant region comprises a capacitive element which changes capacitance in proportion to its change in shape; and wherein the second region comprises an inductive coil electrically coupled to said capacitive element to form a resonant circuit; and wherein the control unit includes:
    means for generating an activation signal as an electromagnetic signal that varies over a predetermined frequency range to cause said resonant circuit to resonate; and
    means for measuring the resonant frequency of said resonant circuit which is representative of the intraocular pressure of the eye.

33. The tonometer system of claim 32 wherein the electromagnetic signal is generated to vary over the frequency range during the predetermined time interval.

34. The tonometer system of claim 32 wherein the control unit includes means for generating the electromagnetic signal superimposed on the non-invasive force signal.

35. The tonometer system of claim 27 wherein the control unit includes a processing means for measuring signals representative of intraocular pressure at different times during the predetermined time interval; and a memory for storing the signals representative of the intraocular pressure measured at said different times.

36. The tonometer system of claim 35 wherein the control unit includes means for processing the stored measured signals representative of intraocular pressure to determine a resultant intraocular pressure (IOP) measurement.

37. The tonometer system of claim 36 wherein the control unit includes means for time marking each resultant IOP measurement with a measurement time and for storing said resultant IOP measurements with their corresponding measurement times in the memory.

38. The tonometer system of claim 37 wherein the control unit includes means for transferring the stored resultant IOP measurements and their corresponding measurement times to another system.

39. The tonometer system of claim 27 wherein the control unit includes a display for displaying the intraocular pressure measurements.

40. The tonometer system of claim 27 wherein the control unit comprises a portable, hand held unit.

41. The tonometer system of claim 27 wherein the control unit is an instrument in a doctor's office.

42. The tonometer system of claim 27 wherein the contact lens comprises a disposable contact lens.

43. A method of measuring intraocular pressure (IOP) of an eye with a flexible contact lens having a microelectromechanical (MEM) sensor affixed thereto; said method comprising the steps of:

disposing said contact lens in close proximity to a surface of said eye with a surface of the MEM sensor in juxtaposition with said eye surface;
    generating a non-invasive force which presses and releases a compliant region of said surface of the MEM sensor against and from said surface of the eye in accordance with a predetermined force vs. time envelope causing said compliant region that is fabricated as an impedance element to change shape and vary in impedance as a result thereof;
    energizing said impedance element a multiplicity of times during said force vs. time envelope;
    determining a pressure representative measurement each time the impedance element is energized; and
    processing said pressure representative measurements to render a resultant IOP measurement.

44. The method of claim 43 wherein the step of generating includes the steps of:
    generating a magnetic field in accordance with a magnetic field strength vs. time envelope; and
    causing a permanent magnet region of the MEM sensor to press the surface of the MEM sensor against the surface of the eye with a force in proportion to the magnetic strength of said field.

45. The method of claim 43 wherein the step of energizing includes the step of:
    energizing an inductive region of the MEM sensor that is connected to the impedance element which is a capacitive region to cause the circuit combination to resonate.

46. The method of claim 45 wherein the step of energizing includes: generating an electromagnetic signal with a frequency that is swept through a frequency range over a predetermined time interval, said resonant frequency of the circuit falling within said frequency range.

47. The method of claim 46 wherein the step of determining includes the steps of determining the resonant frequency of the circuit each time the circuit is energized during the force vs. time envelope, said resonant frequencies being sampled data representative of the IOP of the eye at different times.

48. The method of claim 47 wherein the step of processing includes processing the sampled data resonant frequencies to render a resultant IOP measurement.

49. The method of claim 43 including the steps of: time marking each resultant IOP measurement; and storing each IOP measurement along with its corresponding measurement time.

50. The method of claim 49 including the step of transmitting said stored IOP measurements and their corresponding measurement times to an external site.

51. The method of claim 43 wherein the steps of generating, energizing, determining and processing are performed autonomously by a control unit disposed in proximity to the lens and MEM sensor.

52. The method of claim 51 including the steps of; manually positioning the control unit in close proximity to the lens and MEM sensor for measuring the intraocular pressure of the eye; and manually initiating the steps of generating, energizing, determining and processing.

53. The method of claim 51 including the step of displaying the resultant IOP measurement on the control unit.

54. The method of claim 43 including the step of displaying the resultant IOP measurement.

* * * * *

UNITED STATES PATENT AND TRADEMARK OFFICE
CERTIFICATE OF CORRECTION

PATENT NO.    : 6,447,449 B1
DATED         : September 10, 2002
INVENTOR(S)   : Aaron J. Fleischman et al.

It is certified that error appears in the above-identified patent and that said Letters Patent is hereby corrected as shown below:

Title page,
Item [75], Inventors, after "Cleveland," insert -- Hilel Lewis, Beachwood, Ohio --.

Signed and Sealed this

First Day of April, 2003

JAMES E. ROGAN
*Director of the United States Patent and Trademark Office*